(12) United States Patent
    Christian

(10) Patent No.: US 6,484,322 B2
(45) Date of Patent: Nov. 26, 2002

(54) THERAPEUTIC MAGNET SUPPORT

(76) Inventor: Walter T. Christian, 52820 E. 16$^{th}$ Ave., Strasburg, CO (US) 80136

( * ) Notice: Subject to any disclaimer, the term of this patent is extended or adjusted under 35 U.S.C. 154(b) by 0 days.

(21) Appl. No.: 09/838,009

(22) Filed: Apr. 18, 2001

(65) Prior Publication Data

US 2002/0152539 A1 Oct. 24, 2002

(51) Int. Cl.$^7$ .................................................. A42B 1/24
(52) U.S. Cl. ...................................................... 2/209.13
(58) Field of Search ............................ 2/209.13, 171.2, 2/250, 247, 249, DIG. 11; 601/15

(56) References Cited

U.S. PATENT DOCUMENTS 5,428,844 A * 7/1995 Dougherty ................. 2/209.13
5,993,375 A * 11/1999 Engel ........................... 600/15

* cited by examiner

Primary Examiner—Rodney M. Lindsey
Assistant Examiner—James G Smith
(74) Attorney, Agent, or Firm—Ramon L. Pizarro

(57) ABSTRACT

A magnet support apparatus or cover that attaches to the adjustment band found in many baseball caps or similar headgear that includes a band that extends across the back of the head. In an example of the device, the invention includes a body having a pair of panels, namely a first panel and a second panel. The two panels are joined along an upper edge, and the second panel includes an attachment mechanism that cooperates with the first panel to support the device from the adjustment band.

17 Claims, 3 Drawing Sheets

THERAPEUTIC MAGNET SUPPORT

BACKGROUND OF THE INVENTION (a) Field of the Invention

This invention generally relates to system and method for supporting magnets against certain areas of the head to expose these areas to magnetic fields provided by the magnet or magnets. More particularly, but not by way of limitation, to a system that cooperates with the adjustment band commonly found in baseball caps and the like.

(b) Discussion of Known Art

The use of magnetic fields as part of therapy for various ailments has rapidly gained acceptance in the last few years. Therapy using magnetic fields typically involves exposing selected areas of the body to a magnetic field of desired intensity. A problem associated with achieving the desired strength or intensity of magnetic field is that magnetic fields dissipate at an exponential rate depending on the distance of the magnet or source of the magnetic field. Therefore, in order to achieve the desired exposure to the magnetic field, it is important to ensure proper positioning of the magnets against the body.

The positioning of the magnets against the body has typically been accomplished by providing devices such as mats that are lined with magnets. Other approaches have involved creating articles such as helmets with imbedded magnets. These approaches suffer from significant limitations in that therapy with these devices requires the user to dedicate his or her time solely to the therapy.

Therefore, a review of known devices reveals that there remains a need for a device that allows individuals to position and hold magnets at desired locations over their bodies while being able to carry out routine daily activities. Importantly, there remains a need for a system that allows individuals to position magnets on specific areas of the body, such as the head, to expose these areas to magnetic fields of desired strength.

Furthermore, there remains a need for a system that allows a person to select the strength or intensity of a magnetic field directed at specific location on a person's head.

Still further, it has been discovered that certain regions of the head, particularly the back of the head, preferably just below the inion and at or above the occiput area of the head, are particularly desirable areas for positioning magnets to be used for therapy. Positioning the negative pole of a strong magnet at this area is not difficult, but known devices for supporting the magnets at these locations limit the individuals mobility. Thus, there remains a need for a simple, unobtrusive device that allows an individual to position a magnet near the inion and acciput areas of the head.

SUMMARY

It has been discovered that the problems left unanswered by known art can be solved by providing a magnet support apparatus that attaches to the adjustment band found in many baseball caps or similar headgear that includes a band that extends across the back of the head. In an example of the device, the invention includes a body having a pair of panels, namely a first panel and a second panel. The two panels are joined along an upper edge, and the second panel includes an attachment mechanism that cooperates with the first panel to support the device from the adjustment band. According to one example of the invention the first panel is made of a flexible material, such as a fabric cloth, and includes at least one pocket that can hold a magnet. In the example that is used to hold a magnet, the pocket is in the first panel. This pocket may include a closeable aperture that allows replacement of the magnets held by the device, or may simply be sealed shut to keep the magnet inside and ensure that users do not flip the magnet within the pocket, exposing the individual to the wrong pole of the magnet. Of course, it is contemplated that having a pocket that provides access to the inside of the pocket is desirable in situations where an individual needs to replace the type or strength of the magnet being used.

It is further contemplated that the attachment mechanism that allows the two panels to cooperate with one another to support the device from a baseball cap include sections of hook and loop material that allow the device to be looped around the adjustment band. The sections of hook and loop material would be placed on free edges of the first panel and the second panel, and then used to attach the free edges to one another to complete the loop around the adjustment band of the hat.

The upper edges of the panel may be defined from a fold line where the two panels are joined together. Additionally, it is contemplated that two separate panels may be joined by sections of hook and loop material on both the upper edges as well as on the lower edges of the panels.

It should also be understood that while the above and other advantages and results of the present invention will become apparent to those skilled in the art from the following detailed description and accompanying drawings, showing the contemplated novel construction, combinations and elements as herein described, and more particularly defined by the appended claims, it should be clearly understood that changes in the precise embodiments of the herein disclosed invention are meant to be included within the scope of the claims, except insofar as they may be precluded by the prior art.

DRAWINGS

The accompanying drawings illustrate preferred embodiments of the present invention according to the best mode presently devised for making and using the instant invention, and in which.

DETAILED DESCRIPTION OF PREFERRED EXEMPLAR EMBODIMENTS

While the invention will be described and disclosed here in connection with certain preferred embodiments, the description is not intended to limit the invention to the specific embodiments shown and described here, but rather the invention is intended to cover all alternative embodiments and modifications that fall within the spirit and scope of the invention as defined by the claims included herein as well as any equivalents of the disclosed and claimed invention.

Figure 1:
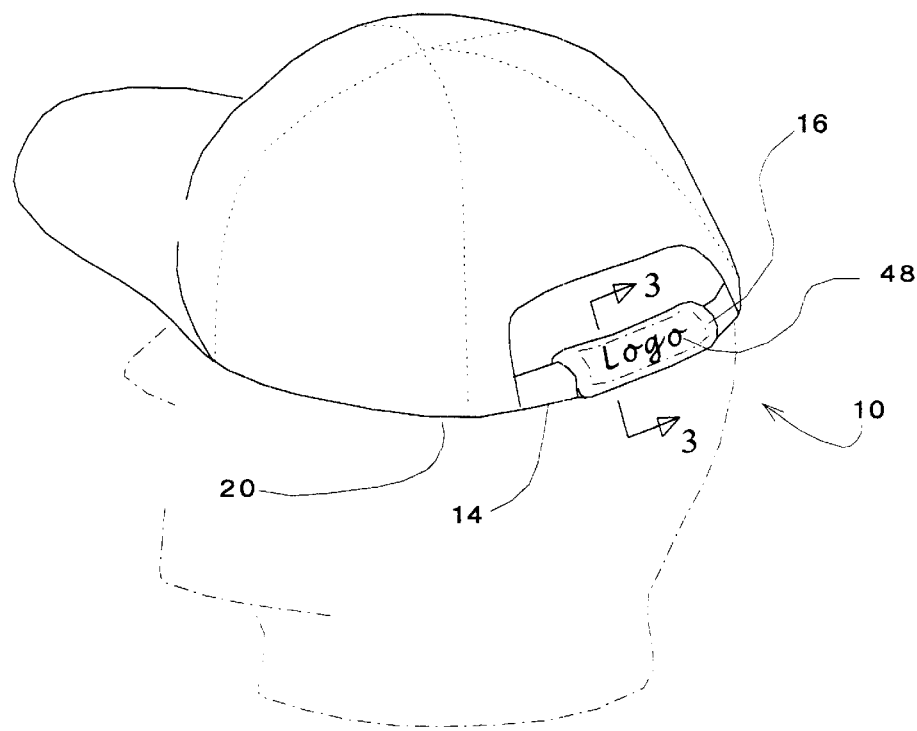
FIG. 1 is a perspective view of an embodiment of the invention used on the adjustment band of a baseball cap.

Turning now to FIG. 1 where a cover device 10 for supporting a magnet 12 against a person's head has been illustrated. The example illustrated in FIG. 1 shows the cover device 10 as being adapted for use over an adjustment band 14 on a hat 16. These adjustment bands 14 are often found on the rear portion of hats, such as baseball caps, hard hats and other headgear. It is contemplated that the adjustment band 14 will be of a width 18 and will extend along a lower edge 20 of the hat 16.

Figure 2:
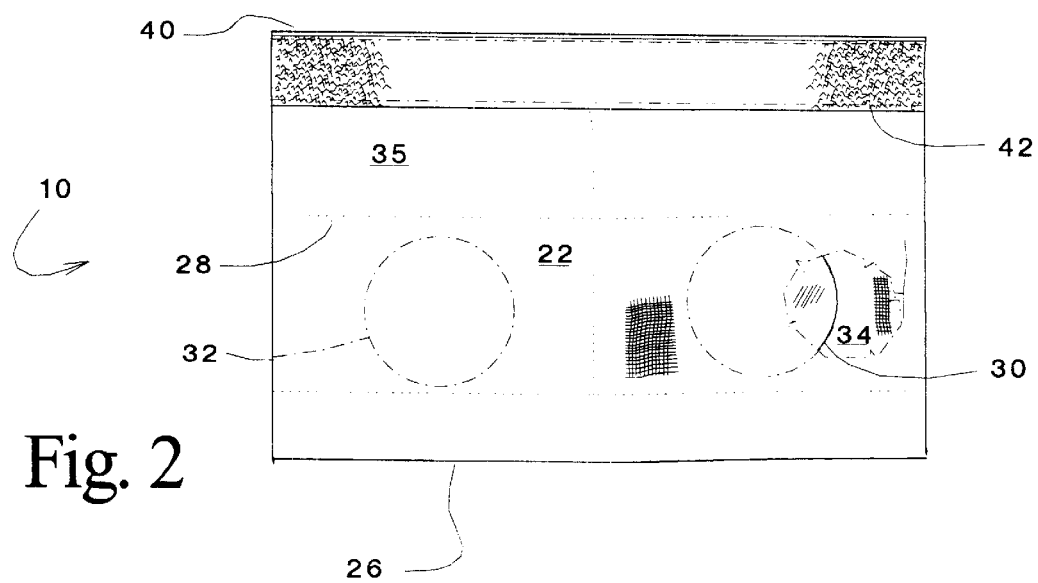
FIG. 2 is a plan view of the example illustrated in FIG. 1.

Turning now to FIG. 2, it will be understood that the example of the cover device 10 illustrated in this figure includes a first panel 22 that includes an upper surface 24, a lower edge 26 and an upper edge 28. As can be understood from FIGS. 1, 2, and 3, it is contemplated that the first panel 22 will be adapted for extending over at least part of the adjustment band 14. A magnet 30 is connected to the first panel 22. However, it is important to note that in order to achieve increased therapeutic effect from magnetic fields, it is contemplated that the magnet 30 will be accompanied by a second magnet 32 that is also supported by the first panel 22.

It has been discovered that by supporting the magnets from the adjustment band 14, the magnetic field generated by the magnets will be positioned at a location that has been found to yield therapeutic effects from the magnetic field. See, e.g., Biomagnetic Handbook A Guide to Medical Magnetics The Energy Medicine of Tomorrow, by William H. Philpott, M.D., and Sharon Taplin, incorporated herein by reference. Thus, the disclosed invention makes use of the adjustment band to position the magnets in the occiput region, and below the inion region of the human head.

The magnets may be supported by simply fastening or adhering the magnets to the fist panel 22. However, it is contemplated that at least one pocket 34 will be incorporated into the first panel 22 to support the magnets. The pockets 34 may have an aperture that allows removal and replacement of the magnets to allow laundering of the cover device 10.

It is further contemplated that the first panel 22 will be attached to a second panel 35 along an upper surface 38 of the second panel 35. The second panel 35 will also include a lower edge 40 that will cooperate with the lower edge 26 of the first panel 22 to retain the cover device 10 over the adjustment band 14 and keep the magnets over the appropriate location at or near the occiput region of the head.

Figure 3:
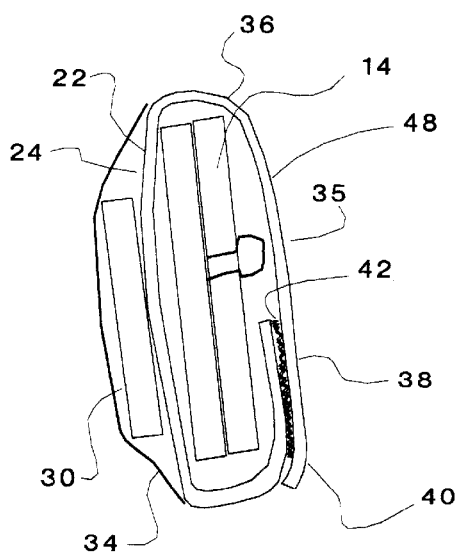
FIG. 3 is a sectional view of the example illustrated in FIG. 1, the view taken long the location indicated and in the direction shown on FIG. 1.

The cooperation between the lower edge 26 of the first panel and the lower edge 40 of the second panel 35 may be carried out by providing areas of hook and loop material 42 at locations near the lower edge 26 of the first panel and the lower edge 40 of the second panel 35. Thus, as shown in FIGS. 2 and 3, it is contemplated that the cover device may be made of fabric or other flexible material, and wrapped around the adjustment band 14 so that the hook and loop material 42 on the lower edge 26 of the first panel and the lower edge 40 of the second panel 35 can met to secure the cover device 10 around the adjustment band 14.

Figure 6:
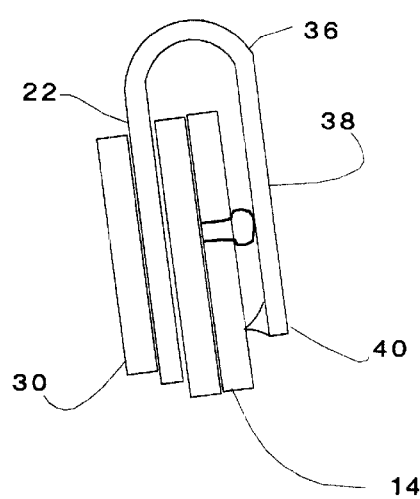
FIG. 6 is another example of an embodiment of the disclosed invention. The figure illustrates the use of preformed resilient sheet, such as of a plastic material, to create the disclosed invention.
Figure 4:
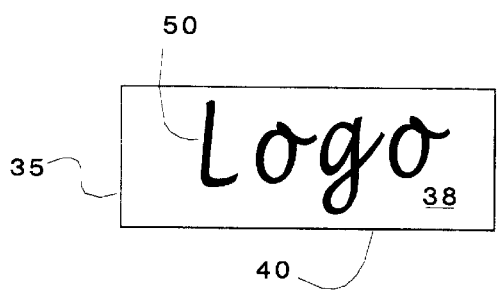
FIG. 4 illustrates the first sheet used in the disclosed invention. The view illustrates the mounting of the magnets on the first sheet.
Figure 5:
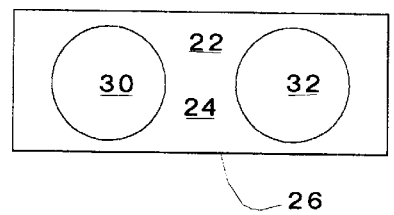
FIG. 5 illustrates the second sheet used with the disclosed invention.

FIG. 6 illustrates that it is contemplated that the first panel 22 and the second panel 35 may be made of a resilient material, such as plastics, including polymer based, moldable magnets, and the lower edge 26 of the first panel and the lower edge 40 of the second panel 35 are urged towards one another through the resilience of these panels when these panels are placed around the adjustment band 14. The magnets 30 and 32 may simply be glued or fastened to the first panel 22 of this embodiment. Thus, FIGS. 4 and 5 illustrate an example of the use of resilient sheets to form the first panel 22 and the second panel 35, and the positioning of the magnets on the second panel 35. It is also important to note that the examples shown in FIGS. 4 and 5 may be made as completely separate sheets with pockets and of fabric or flexible material, and the upper edges and the lower edges of the sheets having sections of hook and loop material, so that the two sheets may be used to sandwich the adjustable strap 14 between them.

Figure 7:
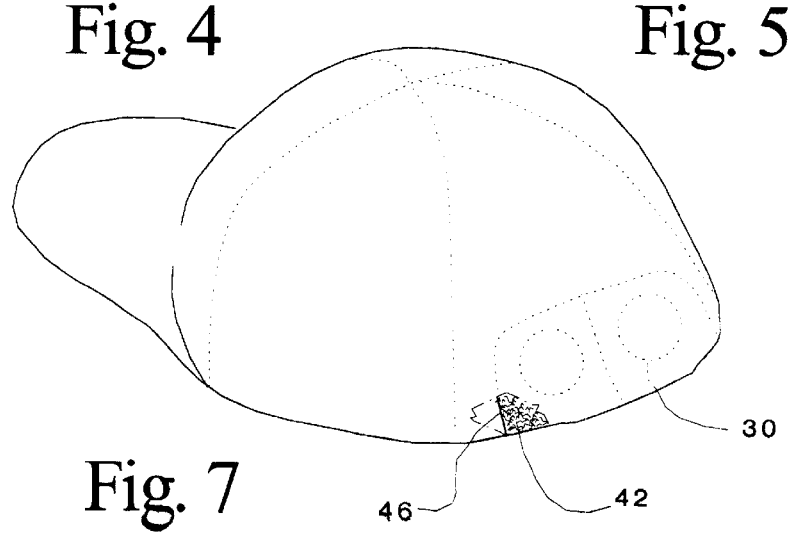
FIG. 7 is yet another example of a device used to practice the principles taught herein. The example illustrates a cap or hat with pockets that support magnets, so that the magnets will be positioned over the desired regions of the back of the head while the hat is worn by a person.

In yet another variation, illustrated in FIG. 7, the hat 44 is of the fitted type, without an adjustable band. In order to use the hat 44 for supporting magnets over the occiput area of the head, at least one pocket 46 has been incorporated into the hat 44, the pocket holding the magnets needed for providing the necessary magnetic field. It is important to note, that it is contemplated that the pocket 46 of this example may be part of a separate panel with hook and loop material, and the inside of the hat 44 would include mating hook and loop material, thus allowing the pocket 46 to be held against the back of the hat 44 for wear and exposure to the magnetic field or simply removed to allow the hat to be worn in a conventional manner.

Figure 8:
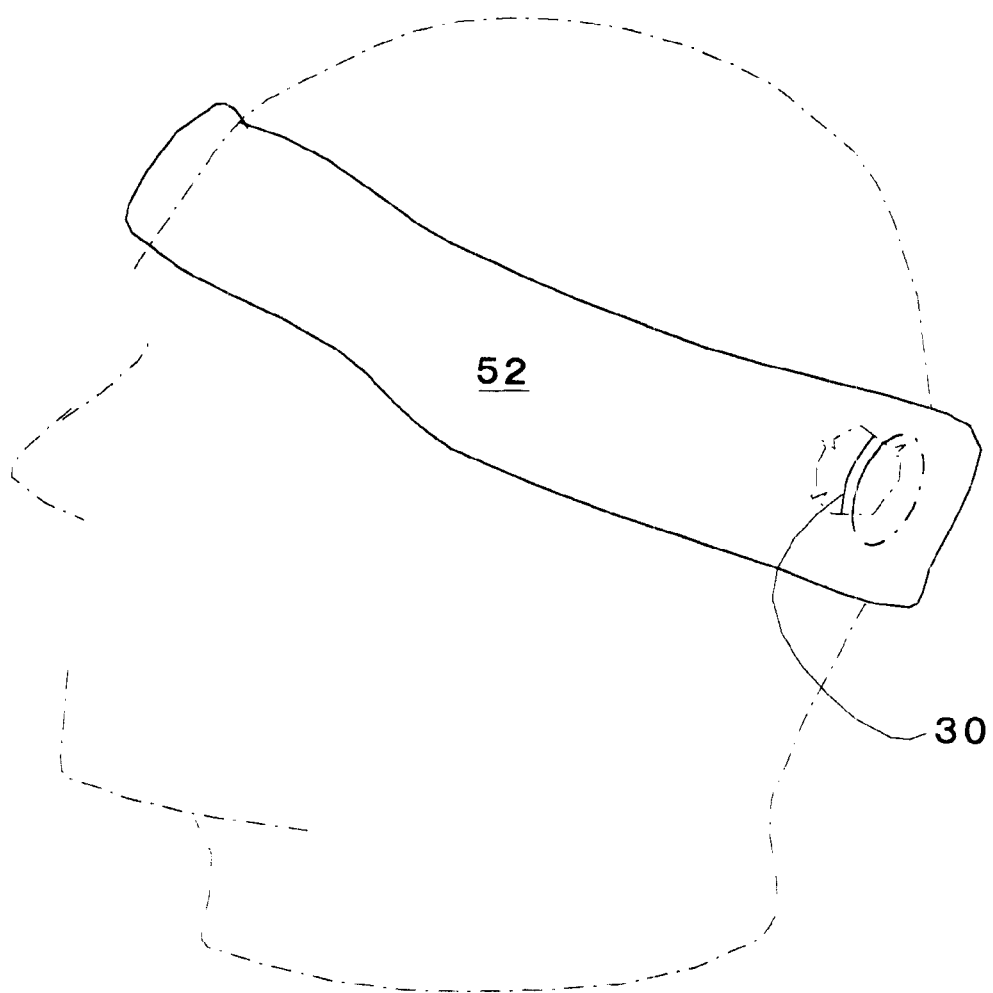
FIG. 8 illustrates a headband, such as a sports headband, that incorporates magnets, so that the magnets may be positioned at desired locations on the head, while being unobtrusive.

Turning now to FIG. 8, it will be understood that the principles taught herein may also be used to use a headband 52 as a support for the magnets. In this example the headband 52 would be incorporate pockets or other support mechanisms, such as hook and loop material as described in conjunction with FIG. 7, or glues or mechanical fastening or sewing mechanisms to support the magnets.

Turning once again to FIGS. 1 and 4, it will be understood that the second panel will include an external surface 48 that will support indicia 50. Thus the cover sleeve will serve to display a message or logo while the hat is worn. Still further, it is contemplated that the cover device will ensure that the mating components of the adjustment band 14 will remain secure, so that the hat will not be accidentally lost. Still further, it is contemplated that the cover device 10 will prevent entanglement of the adjustment mechanism of the adjustable band 14 from becoming entangled with the user's hair. Still further, it is contemplated that bandoleer style pockets may be incorporated into the second panel to support items such as golf tees, pencils, and so on.

Thus it can be appreciated that the above-described embodiments are illustrative of just a few of the numerous variations of arrangements of the disclosed elements used to carry out the disclosed invention. Moreover, while the invention has been particularly shown, described and illustrated in detail with reference to preferred embodiments and modifications thereof, it should be understood that the foregoing and other modifications are exemplary only, and that equivalent changes in form and detail may be made without departing from the true spirit and scope of the invention as claimed, except as precluded by the prior art.

What is claimed is:

1. A cover device for use over an adjustment band on a hat, the adjustment band being of a width and extending along a lower edge of the hat, the cover device comprising:

A first panel having an upper surface, a lower edge and an upper edge the first panel being adapted for extending over the adjustment band, so that the lower edge of the first panel and the upper edge of the first panel are separated by a distance that is approximately equal to the width of the adjustment band;

A magnet supported from said first panel;

A second panel, the second panel having an external surface, most of the external surface of the second panel extend from the first panel in a non-overlapping manner, a lower edge and an upper edge, the upper edge of the first panel being joined to the upper edge of the second panel, the lower edge of the second panel being adapted for cooperating with the lower edge of the first panel so that the cover device is supported around the adjustment band.

2. A cover device according to claim 1 wherein said first panel includes a pair of pockets, each pocket holding a magnet.

3. A cover device according to claim 1, wherein said first panel and said second panel are made from a resilient material.

4. A cover device according to claim 1 wherein said external surface of the second panel supports indicia, so that the cover device displays a message while the hat is worn.

5. A cover device according to claim 1 wherein said lower edge of said first panel and said lower edge of said second panel each include a section of hook and loop material to allow the lower edge of the first panel to attach to the lower edge of he second panel.

6. A cover device for supporting a magnet against a person's head, the cover device being adapted for use over an adjustment band on a hat, the adjustment band being of a width and extending along a lower edge of the hat, the cover device comprising:

A first panel having an upper surface, a lower edge and an upper edge, the first panel being adapted for extending over at least a portion the adjustment band;

At least one magnet mounted from the first panel; and

A second panel, the second panel having an external surface, a lower edge and an upper edge, the upper edge of the first panel being joined to the upper edge of the second panel in a manner that allows the second panel to extend beyond the first panel, so that the second panel is not entirely overlapped by the first panel, the lower edge of the second panel being adapted for cooperating with the lower edge of the first panel so that the cover device is supported around the adjustment band.

7. A cover device according to claim 6 wherein said first panel includes at least one pocket and said magnet is supported within said pocket.

8. A cover device according to claim 6 wherein said first panel includes a pair of pockets, each pocket holding a magnet.

9. A cover device according to claim 6, wherein said first panel and said second panel are made from a resilient material, and said first panel and said second panel being attached to one another, so that the resiliency of the first panel and the resiliency of the second panel is used to urge the second panel towards the first panel to support the cover device over the adjustment band.

10. A cover device according to claim 7 wherein said external surface of the second panel supports indicia, so that the cover device displays a message while the hat is worn.

11. A cover device according to claim 10 wherein said lower edge of said first panel and said lower edge of said second panel each include a section of hook and loop material to allow the lower edge of the first panel to attach to the lower edge of he second panel.

12. A method for adapting a hat so that the hat serves to expose selected areas of a person's head to a magnetic field, the hat having, an opening for accepting a persons head and an adjustment strap for adjusting the hat for accommodating the person's head, the method comprising:

providing a cover device comprising:
A first panel having an upper surface, a lower edge and an upper edge, the first panel being adapted for extending over the adjustment band, so that the lower edge of the first panel and the upper edge of the first panel are separated by a distance that is approximately equal to the width of the adjustment band;
A second panel, the second panel having an external surface, a lower edge and an upper edge, the upper edge of the first panel being joined to the upper edge of the second panel, the lower edge of the second panel being adapted for releasable attachment to the lower edge of the first panel;

supporting at least one magnet with said first panel;
placing said cover device over the adjustment strap so that the first panel and the second panel straddle the adjustment strap, and said first panel is closer to the opening for accepting a person's head than the second panel.

13. A method according to claim 12 wherein said first panel includes at least one pocket.

14. A method according to claim 12 wherein said first panel includes a pair of pockets, each pocket holding a magnet.

15. A method according to claim 12, wherein said first panel and said second panel are made from a resilient material.

16. A method according to claim 12 wherein said external surface of the second panel supports indicia, so that the cover device displays a message while the hat is worn.

17. A method according to claim 12 wherein said lower edge of said first panel and said lower edge of said second panel each include a section of hook and loop material, and the method further comprises using the hook and loop material for attaching the lower edge of the first panel to the lower edge of he second panel.

* * * * *